(12) United States Patent
Cinader, Jr. et al.

(10) Patent No.: US 9,339,352 B2
(45) Date of Patent: May 17, 2016

(54) ORTHODONTIC ARTICLE HAVING PARTIALLY HARDENED COMPOSITION AND RELATED METHOD

(75) Inventors: David K. Cinader, Jr., Walnut, CA (US); James D. Christoff, Birchwood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 244 days.

(21) Appl. No.: 12/742,280

(22) PCT Filed: Nov. 10, 2008

(86) PCT No.: PCT/US2008/082952
§ 371 (c)(1),
(2), (4) Date: May 11, 2010

(87) PCT Pub. No.: WO2009/075977
PCT Pub. Date: Jun. 18, 2009

(65) Prior Publication Data
US 2010/0285419 A1 Nov. 11, 2010

Related U.S. Application Data

(60) Provisional application No. 61/013,345, filed on Dec. 13, 2007.

(51) Int. Cl.
*A61C 3/00* (2006.01)
*A61C 7/16* (2006.01)

(52) U.S. Cl.
CPC .......................... *A61C 7/16* (2013.01)

(58) Field of Classification Search
CPC ............ A61C 7/16; A61C 13/08; B29C 65/14
USPC ................................ 433/9; 156/275.5; 264/19
See application file for complete search history.

(56) References Cited

U.S. PATENT DOCUMENTS

| 4,259,075 A | 3/1981 | Yamauchi et al. |
| 4,298,738 A | 11/1981 | Lechtken et al. |
| 4,324,744 A | 4/1982 | Lechtken et al. |
| 4,356,296 A | 10/1982 | Griffith et al. |
| 4,385,109 A | 5/1983 | Lechtken et al. |

(Continued)

FOREIGN PATENT DOCUMENTS

| EP | 0173567 | 3/1986 |
| EP | 0201031 | 11/1986 |

(Continued)

OTHER PUBLICATIONS

International Search Report PCT/US2008/082952, Feb. 4, 2009, 3 pgs.

(Continued)

*Primary Examiner* — Cris L Rodriguez
*Assistant Examiner* — Mirayda A Aponte

(57) ABSTRACT

An orthodontic article is provided for bonding to a tooth structure comprising an orthodontic appliance, a layer of partially hardened hardenable composition adjacent the appliance, and a bonding adhesive adjacent the partially hardened hardenable composition. A method of making an orthodontic article for orthodontic bonding is provided, comprising partially hardening a hardenable composition adjacent the base of an orthodontic appliance.

4 Claims, 4 Drawing Sheets

(56) References Cited

U.S. PATENT DOCUMENTS

| | | | | |
|---|---|---|---|---|
| 4,499,251 | A | 2/1985 | Omura et al. | |
| 4,503,169 | A | 3/1985 | Randklev | |
| 4,537,940 | A | 8/1985 | Omura et al. | |
| 4,539,382 | A | 9/1985 | Omura et al. | |
| 4,642,126 | A | 2/1987 | Zador et al. | |
| 4,648,843 | A | 3/1987 | Mitra | |
| 4,652,274 | A | 3/1987 | Boettcher et al. | |
| 4,665,217 | A | 5/1987 | Reiners et al. | |
| 4,695,251 | A | 9/1987 | Randklev | |
| 4,710,523 | A | 12/1987 | Lechtken et al. | |
| 4,737,593 | A | 4/1988 | Ellrich et al. | |
| 4,752,338 | A | 6/1988 | Reiners et al. | |
| 4,812,118 | A | 3/1989 | Creekmore | |
| 4,872,936 | A | 10/1989 | Engelbrecht | |
| 5,015,180 | A | 5/1991 | Randklev | |
| 5,076,844 | A | 12/1991 | Fock et al. | |
| 5,130,347 | A | 7/1992 | Mitra | |
| 5,172,809 | A | 12/1992 | Jacobs et al. | |
| 5,221,202 | A | 6/1993 | James | |
| 5,328,363 | A | 7/1994 | Chester et al. | |
| 5,354,199 | A | 10/1994 | Jacobs et al. | |
| 5,429,229 | A | 7/1995 | Chester et al. | |
| 5,530,038 | A | 6/1996 | Yamamoto et al. | |
| 5,545,676 | A | 8/1996 | Palazzotto et al. | |
| 5,552,177 | A | 9/1996 | Jacobs et al. | |
| 5,890,892 | A | 4/1999 | Lemchen | |
| 5,971,754 | A | 10/1999 | Sondhi et al. | |
| 6,030,606 | A | 2/2000 | Holmes | |
| 6,126,922 | A * | 10/2000 | Rozzi et al. | 424/49 |
| 6,183,249 | B1 * | 2/2001 | Brennan et al. | 433/9 |
| 6,251,963 | B1 | 6/2001 | Kohler et al. | |
| 6,302,688 | B1 | 10/2001 | Jordan et al. | |
| 6,387,981 | B1 | 5/2002 | Zhang et al. | |
| 6,458,868 | B1 | 10/2002 | Okada et al. | |
| 6,482,002 | B2 | 11/2002 | Jordan et al. | |
| 6,528,555 | B1 | 3/2003 | Nikutowski et al. | |
| 6,572,693 | B1 | 6/2003 | Wu et al. | |
| 6,624,236 | B1 | 9/2003 | Bissinger et al. | |
| 6,765,036 | B2 | 7/2004 | Dede et al. | |
| 6,852,795 | B2 | 2/2005 | Bissinger et al. | |
| 6,852,822 | B1 | 2/2005 | Bissigner et al. | |
| 6,960,079 | B2 | 11/2005 | Brennan et al. | |
| 7,020,963 | B2 | 4/2006 | Cleary et al. | |
| 7,090,721 | B2 | 8/2006 | Craig et al. | |
| 7,090,722 | B2 | 8/2006 | Budd et al. | |
| 7,155,373 | B2 | 12/2006 | Jordan et al. | |
| 7,156,911 | B2 | 1/2007 | Kangas et al. | |
| 7,726,968 | B2 | 6/2010 | Raby et al. | |
| 7,910,632 | B2 * | 3/2011 | Cinader et al. | 523/118 |
| 2004/0206932 | A1 | 10/2004 | Abuelyaman | |
| 2004/0219471 | A1 | 11/2004 | Cleary et al. | |
| 2004/0219473 | A1 | 11/2004 | Cleary et al. | |
| 2005/0136370 | A1 * | 6/2005 | Brennan et al. | 433/9 |
| 2005/0256223 | A1 | 11/2005 | Kolb et al. | |
| 2006/0134580 | A1 | 6/2006 | Raby et al. | |
| 2006/0223021 | A1 | 10/2006 | Cinader, Jr. et al. | |
| 2006/0223031 | A1 * | 10/2006 | Cinader et al. | 433/213 |
| 2007/0031774 | A1 | 2/2007 | Cinader, Jr. et al. | |
| 2007/0287120 | A1 | 12/2007 | Cinader et al. | |
| 2007/0287121 | A1 | 12/2007 | Cinader et al. | |
| 2008/0096150 | A1 * | 4/2008 | Cinader | 433/9 |
| 2008/0233528 | A1 | 9/2008 | Kim et al. | |

FOREIGN PATENT DOCUMENTS

| | | |
|---|---|---|
| EP | 0201778 | 11/1986 |
| EP | 0373384 | 6/1990 |
| EP | 0712622 | 5/1996 |
| EP | 1051961 | 11/2000 |
| WO | WO 00/38169 | 6/2000 |
| WO | WO 00/42092 | 7/2000 |
| WO | WO 0069393 A1 * | 11/2000 |
| WO | WO 01/07444 | 2/2001 |
| WO | WO 01/30305 | 5/2001 |
| WO | WO 01/30306 | 5/2001 |
| WO | WO 01/30307 | 5/2001 |
| WO | WO 01/92271 | 12/2001 |
| WO | WO 02/089693 | 11/2002 |
| WO | WO 03/063804 | 8/2003 |
| WO | WO 2005/039433 | 5/2005 |
| WO | WO 2009/045752 | 4/2009 |

OTHER PUBLICATIONS

Schmidlin et al., Bonding of Brackets Using a Caries-Protective Adhesive Patch; Journal of Dentistry 36 (2008) 125-129.

* cited by examiner

ORTHODONTIC ARTICLE HAVING PARTIALLY HARDENED COMPOSITION AND RELATED METHOD

CROSS REFERENCE TO RELATED APPLICATIONS

This application is a national stage filing under 35 U.S.C. 371 of PCT/US2008/082952, filed Nov. 10, 2008, which claims priority to U.S. Provisional Application No. 61/013,345, filed Dec. 13, 2007, the disclosure of which is incorporated by reference in its entirety herein.

TECHNICAL FIELD

Orthodontic articles such as brackets and methods for bonding them are provided. More particularly, orthodontic articles including a partially hardened hardenable composition, and methods for bonding them, are provided.

BACKGROUND

Orthodontic treatment involves movement of malpositioned teeth to desired locations in the oral cavity. One common type of orthodontic treatment involves the use of small, slotted orthodontic appliances known as brackets. The brackets are fixed to the patient's teeth and an archwire is placed in the slot of each bracket. The archwire forms a track to guide movement of teeth to desired locations. The ends of orthodontic archwires are often connected to small orthodontic appliances known as buccal tubes that are, in turn, secured to the patient's molar teeth. In many instances, a set of brackets, buccal tubes and an archwire is provided for each of the patient's upper and lower dental arches. The brackets, buccal tubes and archwires are commonly collectively referred to as "braces".

Orthodontic appliances that are adapted to be adhesively bonded to the patient's teeth can be placed and fixed to the teeth using, for example, one of two techniques known as direct bonding and indirect bonding.

In general, direct bonding techniques involve the serial placement of individual adhesive-coated orthodontic appliances, such as brackets, onto a patient's tooth surface by an orthodontist. Typically, one bracket at a time is placed onto a patient's tooth surface until all of the brackets required for treatment are placed on the teeth. Orthodontic brackets can be manufactured with a layer or coating of orthodontic adhesive on the base of each bracket. Alternatively, a layer or coating of orthodontic adhesive can be applied to the base of each bracket by the orthodontist immediately before the bracket is placed onto a tooth surface. In direct orthodontic bonding, the layer or coating of orthodontic adhesive on the appliance is not hardened until after the appliance is placed on a tooth surface. The layer or coating of orthodontic adhesive does not have a contour that is a negative replica of the tooth surface until the adhesive has been placed in contact with the tooth surface. Direct bonding techniques have been used to place and fix a single orthodontic appliance or many orthodontic appliances in a patient's oral cavity.

In general, indirect bonding techniques involve the use of a placement device or transfer apparatus having a shape that matches the configuration of at least part of the patient's dental arch. One type of placement device includes a "transfer tray" and typically has a cavity for receiving a number of teeth simultaneously. A set of orthodontic appliances such as brackets are releasably connected to (for example, embedded in) the tray at certain, predetermined locations. When the tray with embedded orthodontic appliances is placed over the matching portions of the patient's dental arch, each appliance is ultimately positioned on the patient's teeth at the proper location.

Before the tray is formed, the orthodontic appliances are fixed to replica teeth of a model (typically a "stone model") of the patient's dental arch. Typically, an orthodontic adhesive is applied to the orthodontic brackets, the brackets are pressed onto the replica teeth, and the orthodontic adhesive is fully hardened using, for example, an orthodontic curing light. This fully hardened orthodontic adhesive can remain on the orthodontic appliance when it is removed from the replica teeth and can serve as a "custom base" for bonding the appliances to the patient's teeth.

With indirect bonding techniques, the transfer apparatus helps to locate the appliances in their proper, intended positions so that individual adjustment of each appliance on the surface of the tooth before bonding is unnecessary. The placement accuracy of the orthodontic appliances that is often afforded by indirect bonding techniques helps ensure that the patient's teeth are moved to their proper, intended positions by the conclusion of orthodontic treatment.

SUMMARY

As noted above, in orthodontic direct bonding, the hardenable orthodontic adhesive on the appliance is not hardened until after the appliance is placed on a tooth surface. Thus, the hardenable orthodontic adhesive does not have a contour that is a negative replica of the tooth surface until the adhesive has been placed in contact with the tooth surface. The adhesive can be unevenly deformed as the appliance is placed on the tooth, ultimately leading to a weakened or unreliable bond between the tooth structure and the appliance. As noted above, in orthodontic indirect bonding, the fully hardened adhesive used to bond the orthodontic appliances to the stone model can remain on the base of the appliances after detachment from the stone model. The adhesive can then serve as a "custom base" having a concave contour that replicates the convex contour of the previous attachment location of the stone model, as well as the convex configuration of the intended mounting location of the appliances on the patient's teeth. However, bonding orthodontic appliances to a replica plaster or "stone" model can result in a custom base that, when later bonded to a tooth structure, can lead to a weakened or unreliable bond between the tooth structure and the appliance having the custom base thereon. Thus, there is a need for articles and methods for direct and indirect bonding of orthodontic appliances that provide reliable and strong bonds between the appliance and a tooth structure.

Articles and methods are provided for direct and indirect bonding of orthodontic appliances having a partially hardened hardenable composition thereon. The hardenable composition is partially hardened across its extent, even when the orthodontic appliance is made of a material that is opaque to the transmission of actinic radiation.

In one aspect, an orthodontic article for bonding to a tooth structure is provided. The orthodontic article comprises an orthodontic appliance having a base, a partially hardened hardenable composition adjacent the base, and a bonding adhesive adjacent the partially hardened hardenable composition. At least one of the base or the partially hardened hardenable composition has a contour of a negative replica of at least a portion of the tooth structure.

In another aspect, a method of bonding an orthodontic article to a tooth structure is provided. The method comprises applying a hardenable composition to the base of an orthodontic appliance, partially hardening the hardenable composition to provide a partially hardened hardenable composition, and advancing the orthodontic appliance with the partially hardened hardenable composition toward the tooth structure.

In yet another aspect, a method of making an article for orthodontic bonding is provided. The method comprises applying a hardenable composition to the base of an orthodontic appliance, and partially hardening the hardenable composition to provide a partially hardened hardenable composition. At least one of the base or a surface of the partially hardened hardenable composition has a contour of a negative replica of at least a portion of a tooth structure.

This summary is not intended to describe each and every embodiment or implementation. Further embodiments, features, and advantages will be apparent from the following detailed description thereof, from the drawings, and from the claims.

DETAILED DESCRIPTION

Figure 1A:
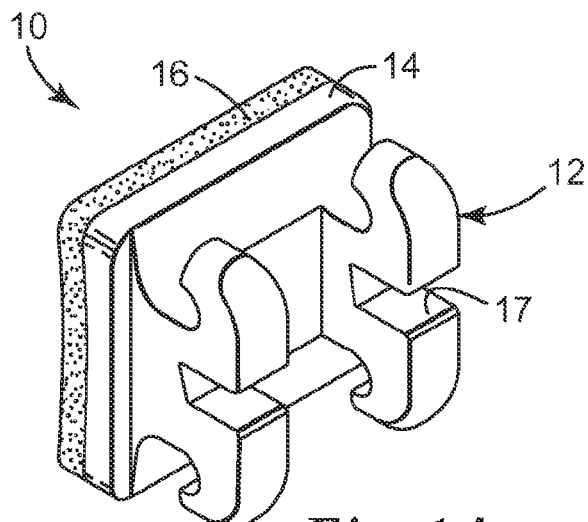
FIG. 1A is a perspective view of an orthodontic article that has a hardenable composition adjacent the substantially flat or planar base of the article.

In several places throughout the application, guidance is provided through lists of examples, which examples can be used in various combinations. In each instance, the recited list serves only as a representative group and should not be interpreted as an exclusive list.

Any recitation of numerical ranges by endpoints includes all numbers subsumed within that range (e.g., 1 to 5 includes 1, 1.5, 2, 2.75, 3, 3.80, 4, 5, etc.).

The terms "a," "an," "the," "at least one," and "one or more" are used interchangeably. Thus, for example, method comprising the step of providing "an" orthodontic appliance can be interpreted to mean that the method comprises the step of providing "one or more" orthodontic appliances.

The term "partially hardened" refers to a partial state of hardening of a hardenable composition, i.e., that the partially hardened hardenable composition is capable of, or can undergo, further hardening.

Various aspects and embodiments of the invention are described below.

Hardenable compositions useful in the present invention include hardenable compositions in the form of light curable adhesives. In some embodiments, the adhesives are light curable dental or orthodontic adhesives. Hardenable compositions typically include a hardenable component and an initiator for initiating hardening of the hardenable composition. Hardenable compositions can include one or more of an acidic component (for example, having phosphoric acid functionality, phosphonic acid functionality, and/or sulfonic acid functionality) having a $pK_a$ of less than 4.5 (and in certain embodiments less than 4 or even less than 3), a filler, or a photobleachable dye. In some embodiments, the hardenable composition is a self-etching hardenable composition. Useful orthodontic adhesive compositions are disclosed in, for example, U.S. Pat. No. 7,090,721 (Craig et al.), U.S. Pat. No. 6,960,079 (Brennan et al.), U.S. Pat. No. 5,971,754 (Sondhi et al.), U.S. Pat. No. 5,552,177 (Jacobs et al.), U.S. Pat. No. 5,354,199 (Jacobs et al.), U.S. Pat. No. 5,221,202 (James), and U.S. Pat. No. 5,015,180 (Randklev).

Hardenable compositions can include hardenable components (e.g., photopolymerizable compounds) that include ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof.

The hardenable compositions can include compounds having free radically active unsaturated groups that can include monomers, oligomers, and polymers having at least one ethylenically unsaturated group. Suitable compounds contain at least one ethylenically unsaturated group and are capable of undergoing addition polymerization. Such free radically polymerizable compounds include mono-, di- or poly-(meth)acrylates (i.e., acrylates and methacrylates) such as alkyl (meth)acrylates, any of numerous glycol (meth)acrylates, (meth)acrylates of polyols, (meth)acrylamides (i.e., acrylamides and methacrylamides), urethane(meth)acrylates, the bis-(meth)acrylates of polyethylene glycols (e.g., of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), poly(ethylenically unsaturated) carbamoyl isocyanurates such as those disclosed in U.S. Pat. No. 4,648,843 (Mitra), and vinyl compounds such as styrene, and diallyl phthalate. Other suitable free radically polymerizable compounds include siloxane-functional (meth)acrylates as disclosed, for example, in PCT International Patent Application Publication Nos. 00/38619 (Guggenberger et al.), 01/92271 (Weinmann et al.), 01/07444 (Guggenberger et al.), and 00/42092 (Guggenberger et al.), and fluoropolymer-functional (meth)acrylates as disclosed, for example, in U.S. Pat. No. 5,076,844 (Fock et al.), U.S. Pat. No. 4,356,296 (Griffith et al.), and in European Patent Application Publication Nos. 0373384 (Wagenknecht et al.), 0201 031 (Reiners et al.), and 0201778 (Reiners et al.).

The hardenable component can contain a hydroxyl group and an ethylenically unsaturated group in the same molecule. Examples of such materials include hydroxyalkyl(meth)acrylates, such as 2-hydroxyethyl(meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (bisGMA). Mixtures of ethylenically unsaturated compounds can be used if desired.

In certain embodiments hardenable components include PEGDMA (polyethyleneglycol dimethacrylate), bisGMA, UDMA (urethane dimethacrylate), GDMA (glycerol dimethacrylate), TEGDMA (triethyleneglycol dimethacrylate), and bisEMA6 (as described in U.S. Pat. No. 6,030,606 (Holmes)), and NPGDMA (neopentylglycol dimethacrylate). Various combinations of the hardenable components can be used if desired.

Hardenable compositions can include ethylenically unsaturated compounds without acid functionality. Hardenable compositions can include at least 1 weight percent, at least 5 weight percent, at least 10 weight percent, at least 20 weight percent, at least 30 weight percent, at least 40 weight percent, at least 50 weight percent, at least 60 weight percent, at least 70 weight percent, at least 80 weight percent, at least 90 weight percent, at least 95 weight percent, or at least 99 weight percent ethylenically unsaturated compounds without acid functionality, based on the total weight of the unfilled composition. Hardenable compositions can include at most 99 weight percent, at most 95 weight percent, at most 90 weight percent, at most 85 weight percent, at most 80 weight percent, at most 70 weight percent, at most 60 weight percent, at most 50 weight percent, at most 40 weight percent, at most 30 weight percent, at most 25 weight percent, at most 20 weight percent, at most 15 weight percent, at most 10 weight percent, at most 5 weight percent, or at most 1 weight percent ethylenically unsaturated compounds without acid functionality, based on the total weight of the unfilled composition.

Hardenable compositions can include one or more hardenable components in the form of an ethylenically unsaturated compound with acid functionality. As used herein, ethylenically unsaturated compounds with acid functionality is meant to include monomers, oligomers, and polymers having both ethylenic unsaturation and acid and/or acid-precursor functionality. Acid-precursor functionality includes, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds with phosphate, carboxylic acid, sulfonic acid, or phosphonic acid groups, such as glycerol phosphate mono (meth)acrylates, glycerol phosphate di(meth)acrylates, and hydroxyethyl(meth)acrylate (e.g., HEMA) phosphates. Certain compositions include an ethylenically unsaturated compound with acid functionality having at least one P—OH moiety.

Certain of these compounds are obtained, for example, as reaction products of isocyanatoalkyl(meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Patent Application Publication No. 2004/0206932; AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Patent Application Publication Nos. EP 712,622 (Tokuyama Corp.) and EP 1,051,961 (Kuraray Co., Ltd.).

Suitable photoinitiators for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Typical iodonium salts are the diaryl iodonium salts, e.g., diphenyliodonium chloride, diphenyliodonium hexafluorophosphate, and diphenyliodonium tetrafluoroborate. Suitable photosensitizers are monoketones and diketones that absorb some light within a range of 400 nm to 520 nm, such as camphorquinone, benzil, furil, and 3,3,6,6-tetramethylcyclohexanedione. Electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and European Patent Application No. 0173567 (Ying).

The initiator system is present in an amount sufficient to provide the desired rate of hardening. For a photoinitiator, this amount will be dependent in part on the light source, the thickness of the composition to be exposed to actinic radiation, and the extinction coefficient of the photoinitiator. Typically, the initiator system is present in a total amount of at least 0.01 weight percent, at least 0.03 weight percent, or at least 0.05 weight percent, based on the weight of the composition. Typically, the initiator system is present in a total amount of no more than 10 weight percent, no more than 5 weight percent, or no more than 2.5 weight percent, based on the weight of the composition.

Hardenable compositions as described herein can optionally contain fillers. Fillers can be selected from one or more of a wide variety of materials suitable for incorporation in compositions used for dental applications, such as fillers currently used in dental restorative compositions, and the like.

In certain embodiments, the filler is finely divided. The filler can have a unimodal or polymodal (e.g., bimodal) particle size distribution. For some embodiments, the maximum particle size (the largest dimension of a particle, typically, the diameter) of the filler is less than 50 micrometers, less than 20 micrometers, less than 10 micrometers, less than 5 micrometers, less than 1 micrometer, less than 0.5 micrometer, less than 0.1 micrometer, or less than 0.05 micrometer.

The filler can be an inorganic material. Alternatively, the filler can be a crosslinked organic material that is insoluble in the hardenable composition, and can itself be filled with inorganic filler. The filler can be radiopaque or radiolucent. The filler typically is substantially insoluble in water.

Examples of suitable inorganic fillers are naturally occurring or synthetic materials including, but not limited to silicas (e.g., quartz); nitrides (e.g., silicon nitride); glasses and fillers derived from, for example, Zr, Sr, Ce, Sb, Sn, Ba, Zn, and Al; feldspar; borosilicate glass; kaolin; talc; zirconia; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas (from Evonik Degussa Corp., Akron, Ohio) and CAB-O-SIL M5 silica (from Cabot Corp., Tuscola, Ill.)). Examples of suitable organic filler particles include filled or unfilled pulverized polycarbonates, polyepoxides, and the like. Other examples of polymeric fillers are disclosed in U.S. Provisional Patent Application No. 60/976,501.

Suitable fillers include quartz (i.e., silica), submicron silica, zirconia, submicron zirconia, and non-vitreous microparticles of the type described in U.S. Pat. No. 4,503,169 (Randklev). Mixtures of these fillers can also be used, as well as combination fillers made from organic and inorganic materials.

The surface of the filler particles can be treated with a surface modifying agent or with a coupling agent. In some embodiments, the surface modifying agent is a coupling agent. Suitable coupling agents include gamma-methacryloxypropyltrimethoxysilane, gamma-mercaptopropyltriethoxysilane, gamma-aminopropyltrimethoxysilane, and the like. Silane-treated zirconia-silica ($ZrO_2$—$SiO_2$) filler, silane-treated silica filler, silane-treated zirconia filler, and combinations thereof are especially preferred in certain embodiments.

Other suitable fillers are disclosed in U.S. Pat. No. 6,387,981 (Zhang et al.) and U.S. Pat. No. 6,572,693 (Wu et al.) as well as PCT International Publication Nos. 01/30305 (Zhang et al.), 01/30306 (Windisch et al.), 01/30307 (Zhang et al.), and 03/063804 (Wu et al.). Filler components described in these references include nanosized silica particles, nanosized metal oxide particles, and combinations thereof. Nanofillers are also described in U.S. Pat. No. 7,090,721 (Craig et al.), U.S. Pat. No. 7,090,722 (Budd et al.), and U.S. Pat. No. 7,156,911 (Kangas et al); and U.S. Patent Application Publication No. 2005/0256223 (Kolb et al.).

In some embodiments, the hardenable composition includes at least 1 weight percent, at least 2 weight percent, at least 5 weight percent, at least 10 weight percent, at least 15 weight percent, at least 20 weight percent, at least 25 weight percent, at least 30 weight percent, at least 35 weight percent, at least 40 weight percent, at least 45 weight percent, at least 50 weight percent, at least 55 weight percent, at least 60 weight percent, at least 70 weight percent, at least 80 weight percent, or at least 90 weight percent filler, based on the total weight of the hardenable composition. In some embodiments, the hardenable composition includes at most 90 weight percent, at most 80 weight percent, at most 70 weight percent, at most 60 weight percent, at most 50 weight percent, at most 45 weight percent, at most 40 weight percent, at most 35 weight percent, at most 30 weight percent, at most 25 weight percent, at most 20 weight percent, at most 15 weight percent, at most 10 weight percent, at most 5 weight percent, at most 2 weight percent, or at most 1 weight percent filler, based on the total weight of the composition.

Optionally, compositions of the present invention can contain solvents such as alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone), and water.

If desired, the compositions of the invention can contain additives such as indicators, dyes (including photobleachable dyes such as those disclosed in U.S. Pat. No. 6,528,555 (Nikutowski et al.)), pigments, inhibitors, accelerators, viscosity modifiers, wetting agents, buffering agents, stabilizers, and other similar ingredients that will be apparent to those skilled in the art.

Additionally, medicaments or other therapeutic substances can be optionally added to the hardenable compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like. Combination of any of the above additives can also be employed. The selection and amount of any one such additive can be selected by one of skill in the art to accomplish the desired result without undue experimentation.

In various aspects of the present invention, the hardenable composition can be partially hardened by directing sufficient actinic radiation to the hardenable composition to partially harden it. For example, the source of the actinic radiation, the intensity of the actinic radiation, or the exposure time can be independently controlled to partially harden the hardenable composition to a desired extent. The extent of hardening of a partially or fully hardened hardenable composition relates to the degree of cure of the composition, i.e., to a proportion of reactive chemical groups that have reacted, for example when exposed to actinic radiation, to form chemical bonds that increase the molecular weight of the hardenable composition, crosslink the hardenable composition, or both. The degree of cure of a partially hardened hardenable composition can be measurably increased. That is, the proportion of reactive chemical groups that have reacted can be measurably increased when the partially hardened hardenable composition is further exposed to curing conditions such as exposure to actinic radiation. The extent of hardening of the partially hardened hardenable composition can then be determined by comparing the degree of cure of the partially hardened hardenable composition to the degree of cure of the composition wherein the proportion of reacted chemical groups does not appreciably or measurably increase when the composition is further exposed to curing conditions.

The degree of cure of a partially or fully hardened hardenable composition can be determined by methods that can detect chemical groups that can react, for example when exposed to actinic radiation. For example, analytical spectrophotometric methods such as ultraviolet/visible spectrophotometry or infrared spectrophotometry (including Raman, and attenuated total reflectance transmission infrared spectrophotometry) can be used. Other analytical methods, such as $^1H$ or $^{13}C$ nuclear magnetic resonance spectroscopy, can also be useful. In some embodiments, comparison of analytical data from unhardened, partially hardened, and fully hardened hardenable compositions can be used to calculate, for example, the percentage of reactive chemical groups that have reacted to partially harden the hardenable composition. Such comparisons of data from unhardened, partially hardened, and fully hardened hardenable compositions provide information relating to the degree of cure, and thus the extent of hardening, of the composition. In some embodiments, comparison of spectrophotometric analyses of unhardened, partially hardened, and fully hardened hardenable compositions can be used to calculate, for example, the percentage of chemical groups that have not reacted to partially harden the hardenable composition (i.e., the percentage of chemical groups that remain after the composition is partially hardened). Such comparisons can provide an approximate or an exact percentage of chemical groups that remain after the hardenable composition is partially hardened.

One example of a method that can be used to calculate the degree of cure of a partially hardened hardenable composition is to calculate the ratio of the absorbance (determined, for example, spectrophotometrically) of unreacted reactive chemical groups in a partially hardened hardenable composition to the absorbance of unreacted reactive chemical groups in a composition in which the proportion of reacted chemical groups does not appreciably or measurably increase when the composition is further exposed to curing conditions, and multiplying the result by 100.

Typically, a partially hardened hardenable composition is partially cured although, depending on the composition, the extent of hardening and the degree of cure might not be the same. In this context, the term "partially cured" refers to a composition that has measurably partially cured and is capable of, or can undergo, further measurable curing.

Alternatively, the extent of hardening of a partially hardened hardenable composition can be determined by comparisons of measurements of physical properties (such as hardness, modulus, or strength of an adhesive bond to a substrate) of unhardened, partially hardened, and fully hardened hardenable compositions.

The chemical groups that can react to harden the composition include, for example, ethylenically unsaturated groups such as (meth)acrylate groups, (meth)acrylamide groups, and vinyl groups.

Typically, a partially hardened hardenable composition is partially cured but is less than fully cured. A partially hardened hardenable composition can be less than 100 percent, less than 99.9 percent, less than 99.5 percent, less than 99 percent, less than 98 percent, less than 97 percent, less than 96 percent, less than 95 percent, less than 94 percent, less than 93 percent, less than 92 percent, less than 91 percent, less than 90 percent, less than 85 percent, less than 80 percent, less than 70 percent, less than 60 percent, less than 50 percent, less than 40 percent, less than 35 percent, less than 30 percent, less than 25 percent, less than 20 percent, or less than 10 percent cured. A partially hardened hardenable composition can be at most 5 percent, at most 10 percent, at most 15 percent, at most 20 percent, at most 25 percent, at most 30 percent, at most 35 percent, at most 40 percent, at most 45 percent, at most 50 percent, at most 55 percent, at most 60 percent, at most 65 percent, at most 70 percent, at most 75 percent, at most 80 percent, at most 85 percent, at most 90 percent, at most 95 percent, at most 98 percent, or at most 99 percent cured. In some embodiments, the partially hardened hardenable composition is 27 to 94 percent cured.

Typically, substantially all portions of the hardenable composition are partially hardened before the appliance is positioned on a tooth structure. In some embodiments, substantially all portions of the hardenable composition are partially hardened to substantially the same extent. In other embodiments, various portions of the hardenable composition are partially hardened to different extents.

FIG. 1A illustrates one embodiment of orthodontic article 10 including orthodontic appliance 12 having base 14 and hardenable composition 16 adjacent the base. In FIG. 1A, base 14 is illustrated as flat or planar. In some embodiments, base 14 of orthodontic appliance 12 has a contour of a negative replica of at least a portion of a tooth structure.

Figure 1B:
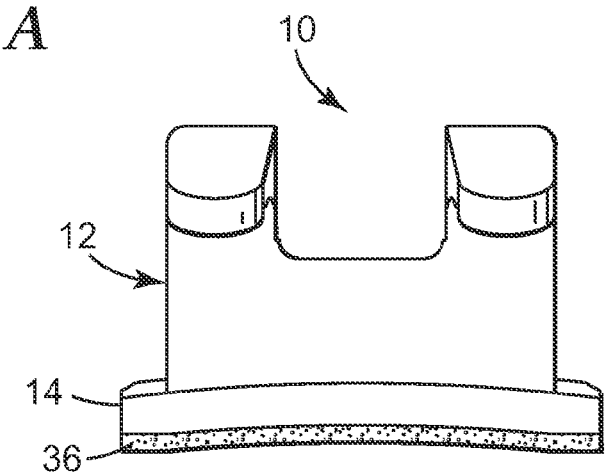
FIG. 1B is a side view of an orthodontic article, similar to that of FIG. 1A, that has a partially hardened hardenable composition adjacent the contoured base of the article.

FIG. 1B illustrates one embodiment of orthodontic article 10 including orthodontic appliance 12 having base 14 and a partially hardened hardenable composition 36 adjacent the base. In FIG. 1B, base 14 is illustrated as having a contour of at least a portion of a tooth structure.

Figure 1C:
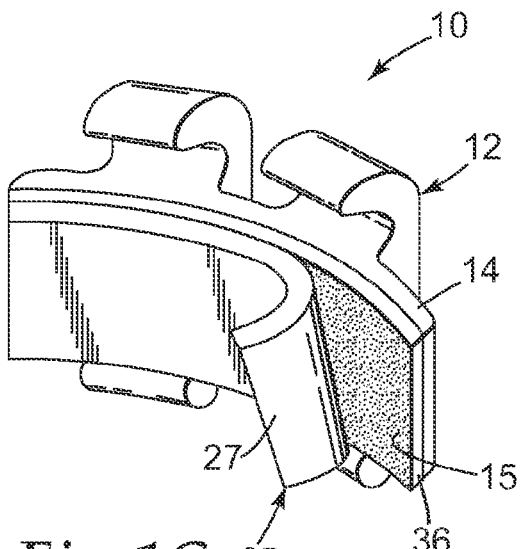
FIG. 1C is a perspective view of an orthodontic article that has a partially hardened hardenable composition adjacent the base of the article and a release substrate.

FIG. 1C illustrates one embodiment of orthodontic article 10 including orthodontic appliance 12 having base 14, partially hardened hardenable composition 36 adjacent the base, and release substrate 25 including surface 27. In the embodiment illustrated, release substrate 25 is adjacent surface 15 of partially hardened hardenable composition 36. Release substrate 25 can comprise any of a number of materials including, for example, polyolefins, poly(vinyl chloride), polyurethanes, and fluorinated polymers such as poly(tetrafluoroethylene). In some embodiments, surface 27 of release substrate 25 comprises a number of pores. In the embodiment illustrated in FIG. 1C, orthodontic appliance 12 is an orthodontic bracket.

In some embodiments, base 14 and partially hardened hardenable composition 36 each have a contour of a negative replica of at least a portion of a tooth structure. In some embodiments, one of partially hardened hardenable composition 36 or base 14 has a contour of a negative replica of at least a portion of a tooth structure. In some embodiments, one of surface 15 or base 14 has a contour of a negative replica of at least a portion of a tooth structure.

The base 14 of orthodontic appliance 12 can be, for example, machined or milled to have a contour of a negative replica of at least a portion of a tooth structure. Alternatively, orthodontic appliance 12 can be molded so that base 14 has a contour of a negative replica of at least a portion of a tooth structure. Digital data can be used to, for example, machine or mill an orthodontic appliance, particularly the base of the appliance, to a shape that comprises a contour of a negative replica of at least a portion of a tooth structure. Alternatively, the digital data can be used to fabricate a mold of at least a portion of the tooth structure, in which an orthodontic appliance can be molded. The base of each orthodontic appliance can have a contour of a negative replica of at least a portion of the structure of a specific tooth, i.e., each base can have a unique contour. Digital data of a patient's teeth for use in making the appliance can be obtained using, for example, an intra-oral scanner. Alternatively, digital data can be obtained by scanning an impression or a stone or polymer model of a patient's dental arch.

The partially hardened hardenable composition can have a contour of a negative replica of at least a portion of a tooth structure. In some embodiments, a hardenable composition is applied to the base of an orthodontic appliance to provide an appliance with a hardenable composition adjacent the base (e.g., as illustrated in FIG. 1A), and actinic radiation is directed toward the hardenable composition using a method, such as a stereolithographic method or laser interference lithography, to partially harden at least pre-selected areas of the hardenable composition so that it has a contour of a negative replica of at least a portion of a tooth structure. Using methods such as stereolithographic method or laser interference lithography, a portion of the hardenable composition (for example, a portion adjacent the base of the orthodontic appliance) is partially hardened so that it has a contour of a negative replica of at least a portion of a tooth structure, and any remaining unhardened hardenable composition can be removed using, for example, a solvent. Alternatively, the hardenable composition can be applied to the base of an orthodontic appliance having a contour of a negative replica of at least a portion of a tooth structure. In this method of partially hardening the hardenable composition, use of a model or replica of the patient's dental arch can be omitted.

In some embodiments, as described below, the hardenable composition adjacent the base of the orthodontic appliance can be placed adjacent or in contact with a replica of at least a portion of a patient's dental arch such that, upon partial hardening, the partially hardened hardenable composition has a contour of a negative replica of at least a portion of a tooth structure. In some embodiments, the partially hardened hardenable composition of each orthodontic appliance can have a contour of a negative replica of at least a portion of the structure of a specific tooth, i.e., each partially hardened hardenable composition can have a unique contour.

The appliances can be placed on the teeth by the orthodontist using a direct bonding procedure. Each appliance can be placed in its proper position on the corresponding tooth.

Figure 2:
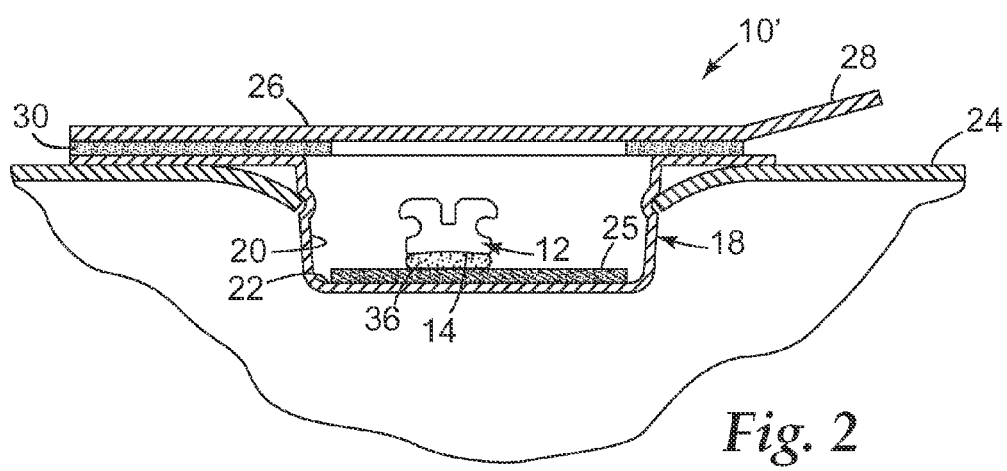
FIG. 2 is a fragmentary view of an orthodontic article.

FIG. 2 illustrates another embodiment of orthodontic article wherein the orthodontic article comprises a container 18 enclosing the orthodontic article. In some embodiments, orthodontic article is a packaged orthodontic article 10'. The packaged orthodontic article 10' includes orthodontic appliance 12 and partially hardened hardenable composition 36 adjacent base 14. The orthodontic appliance 12, illustrated in the form of an orthodontic bracket, and partially hardened hardenable composition 36 are at least partially surrounded by container 18. The exemplary container 18 illustrated in FIG. 2 includes an integrally-molded body with internal wall portions that define a recess or well 20. Well 20 includes side walls and bottom 22. Optionally, the side walls of the well 20 include horizontally extending recesses for engagement with edge structure of carrier 24. Features of suitable carriers are described in U.S. Pat. No. 5,328,363 (Chester et al.). Typically, the orthodontic article includes release substrate 25. In some embodiments, bottom 22 of well 20 comprises a release substrate or, alternatively, a release surface. Typically, packaged orthodontic article 10' includes cover 26 with tab 28, with cover 26 being connected to the container 18 by, for example, adhesive 30. In some embodiments, adhesive 30 forms a seal. Alternatively, a seal can be formed between well 20 and cover 26 by, for example, a heat seal.

Figure 3:
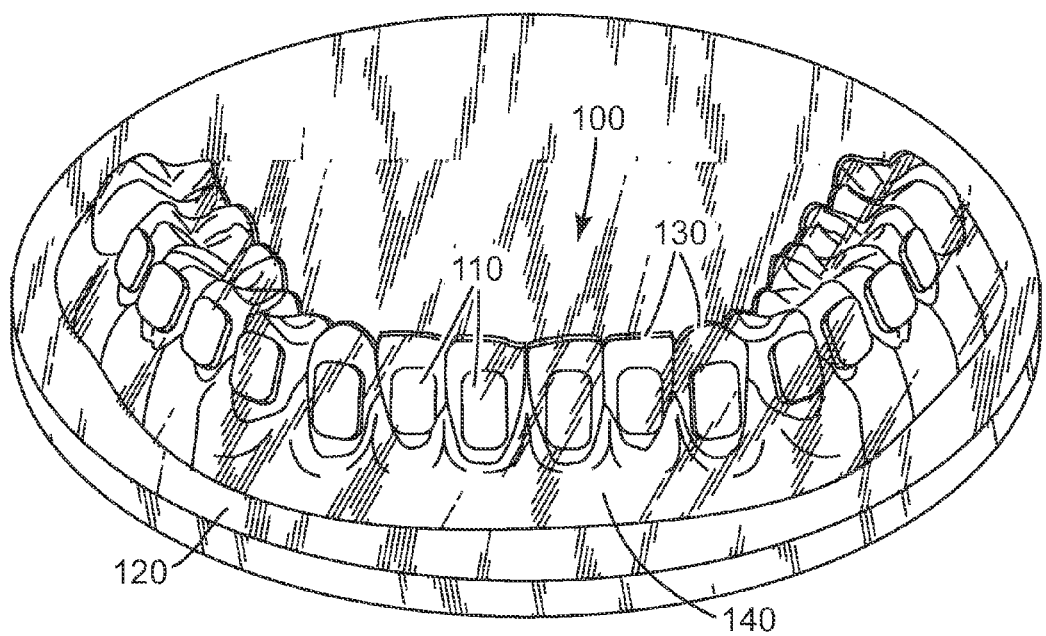
FIG. 3 is a view of a dental arch replica, along with spacer material that has been applied to the replica.

FIG. 3 illustrates a replica 100 of a portion of a dental arch of an orthodontic patient for use in an embodiment of making, for example, a transfer apparatus or transfer assemble for indirect orthodontic bonding. For exemplary purposes, replica 100 represents the patient's lower dental arch. Alternatively, a replica of a patient's upper dental arch or only a portion of a dental arch, such as a quadrant of an arch or only one or two teeth of an arch can be provided. In the embodiment illustrated, replica 100 includes a number of replica teeth 130, corresponding to each tooth of the patient's lower dental arch.

Replica 100 can be made by first taking an impression of the patient's lower dental arch, using dental impression materials such as a hydrocolloid impression material or a vinyl siloxane impression material. Examples of poly(vinyl siloxane) impression materials include those available under the trade designations IMPRINT 3 and POSITION PENTA, both available from 3M ESPE, St. Paul, Minn.

The model or replica 100 can then made from the impression. Optionally, replica 100 can include only replica teeth 130 and sufficient replica gingival tissue 140 to hold the replica teeth 130 together. In some embodiments, replica 100 is a "stone" model made from plaster of Paris. In some embodiments, replica 100 (including replica teeth 130) comprises a material that transmits actinic radiation. Suitable materials include polymers such as epoxy resins that are transparent or translucent when hardened. In some embodiments, the material is optically clear and nonporous. One suitable epoxy resin system is available under the trade designation E-CAST F-82 resin and UCE-302 hardener, both available from United Resin Corp., Royal Oak, Mich. Other suitable materials include polyesters and urethanes.

Alternatively, replica 100 can be made using digital data that is representative of the patient's teeth and adjacent gingival tissue. The digital data can be obtained by use of a hand-held intra-oral scanner or other device known in the art. Alternatively, the digital data can be obtained by scanning an impression or a stone or polymer model. The replica 100 can then be made from the digital data using, for example, a stereo lithographic printer and a material that transmits actinic radiation.

Replica 100 can also be made using digital data in conjunction with a milling process. For example, a computer numeric controlled (CNC) milling machine, similar to the CAD/CAM milling machines sold by Cerec Network of Buelach, Switzerland, can be used to mill replicas made of ceramic, composite or other materials. An intra-oral camera, similar to the cameras associated with the Cerec machines, can be used to obtain digital data representing the shape of the dental arch. The digital data can be used to prepare a replica of at least a portion of a dental arch of an orthodontic patient by a method such as rapid prototyping. Examples of suitable rapid prototyping processes include solid freeform fabrication such as 3D printing processes, stereolithography methods, fused deposition modeling, laminated object manufacturing, laser engineered net shaping, selective laser sintering, shape deposition manufacturing and solid ground curing. In some embodiments, rapid prototyping can include the use of CAD/CAM software to direct a milling machine to mill the dental arch model with alignment guides, occlusal stop members and a tray molding vessel. Such methods are described in U.S. patent application Ser. No. 11/689,845.

Typically, replica 100 is an accurate representation of the patient's oral structure, and replica teeth 130 and replica gingival tissue 140 will each have a configuration and orientation that is identical to the configuration and orientation of the corresponding teeth and gingival tissue of the patient.

Figure 4:
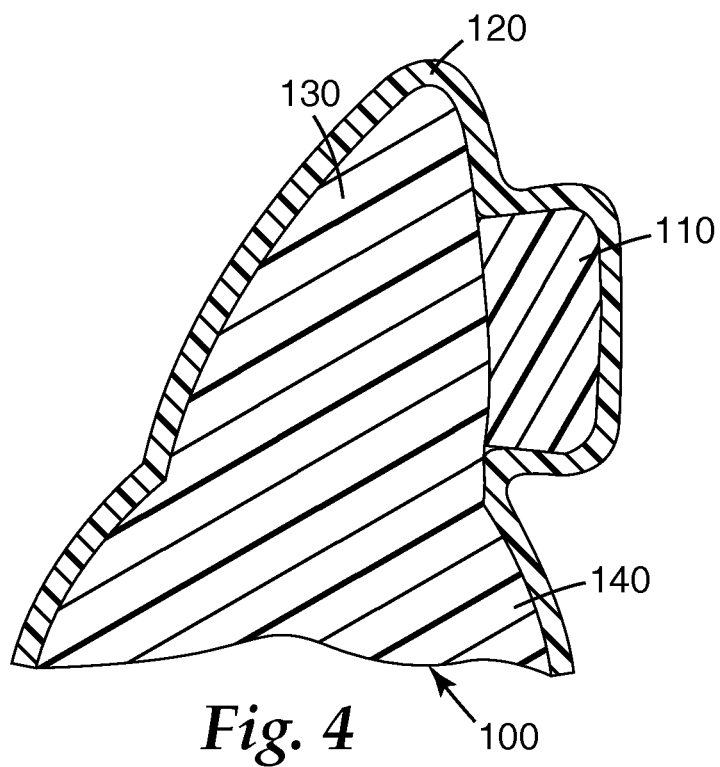
FIG. 4 is an enlarged side cross-sectional view of one of the replica teeth illustrated in FIG. 3 along with the spacer material.

Next and as also shown in FIG. 4, a spacer material is applied to or formed over the replica 100. In this example, the spacer material includes a first spacer material 110 that comprises a series of discrete dabs or pre-formed segments of material that are placed at approximate, pre-determined locations on the replica teeth 130. Each of the dabs or segments of spacer material 110 is placed in a location that corresponds to a subsequent intended location of an orthodontic appliance and has an overall size that is typically at least as large as the base of the selected appliance. Each of the segments of spacer material 110 functions to subsequently provide clearance in a transfer apparatus for receiving an orthodontic appliance.

In some embodiments, the spacer material also includes a sheet of spacer material 120 that preferably extends across a substantial portion of the surfaces of replica teeth 130 and preferably across at least a portion of the surface of replica gingival tissue 140. In some embodiments, and as illustrated in FIG. 4, the sheet spacer material 120 also extends over the segments of spacer material 110. In the illustrated example, the sheet of spacer material 120 extends over the entire buccolabial surface area of replica teeth 130, along the occlusal edge of replica teeth 130 and across the entire lingual side of replica teeth 130, although other constructions are also possible.

Alternatively, spacer material 110, 120 can be provided as an integral unitary section of material. Additionally, the sheet of material 120 (whether alone, or whether integral with the spacer material 110) can be preformed to a configuration that approximates the shape of a dental arch. This construction facilitates subsequent conforming of sheet 120 to replica teeth 130 as will be described below.

The spacer material 110, 120 can be any of a number of materials. A suitable material is a silicone material, such as one available under the trade designation RTV615 from General Electric Co., Wilton, Conn. In some embodiments, dabs of spacer material can be provided by dispensing a quantity of a material from a syringe and then shaping each dab as needed with a hand instrument. In some embodiments, rapid prototyping can be used to prepare spacers 110, as described in U.S. Patent Publication No. 2006/0223031 (Cinader et al.).

Next, a vacuum can be applied to replica 100 and spacer material 110, 120 in order to conform the sheet of spacer material 120 to, or draw the sheet toward, the configuration of replica teeth 130 and replica gingival tissue 140. As used herein, the term "vacuum" refers to any pressure that is lower than atmospheric pressure. Typically, replica 100 along with spacer material 110 is placed on a support having channels communicating with a vacuum pump. The sheet of spacer material 120 is then placed over the replica and the vacuum pump is activated to draw down the sheet of spacer material 120 into conformance with the shape of replica teeth 130 and replica gingival tissue 140.

Figure 5:
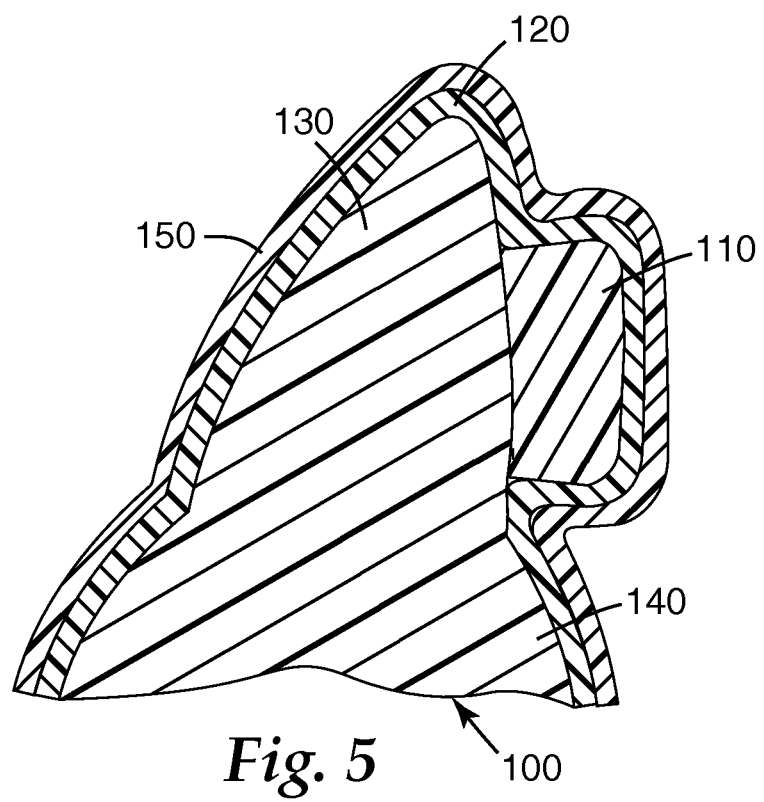
FIG. 5 is an enlarged side cross-sectional view similar to FIG. 4, additionally showing a tray that has been formed over the spacer material.

Subsequently, a tray 150 is formed over the spacer material 110, 120 as illustrated in FIG. 5. Typically, tray 150 is shaped by vacuum forming a sheet of material over the sheet of spacer material 120. A suitable material for tray 150 is a sheet of polycarbonate such as those available under the trade designation MAKROLON from Bayer MaterialScience AG, Leverkusen, Germany, or under the trade designation LEXAN from SABIC Innovative Plastics Holding BV, Pittsfield, Mass. The sheet can have a thickness of, for example, 1.52 millimeters (0.06 inch). Other materials, such as poly (ethyleneterephthalate glycol) ("PETG") can also be used. Heat can be applied during the vacuum forming process in order to facilitate conformance of the sheet to the configuration of spacer material 110, 120. Tray 150 can then be detached from spacer material 110, 120. The spacer material 110, 120 is then detached from replica 100 and is set aside. Excess portions of tray 150 can be trimmed as desired.

In some embodiments, a thin layer of a release agent is then applied to the replica. An example of a suitable release agent is a water soluble polyvinyl alcohol. A suitable release agent is available under the trade designation PA0810 from PTM&W Industries, Inc., Santa Fe Springs, Calif.

Figure 6:
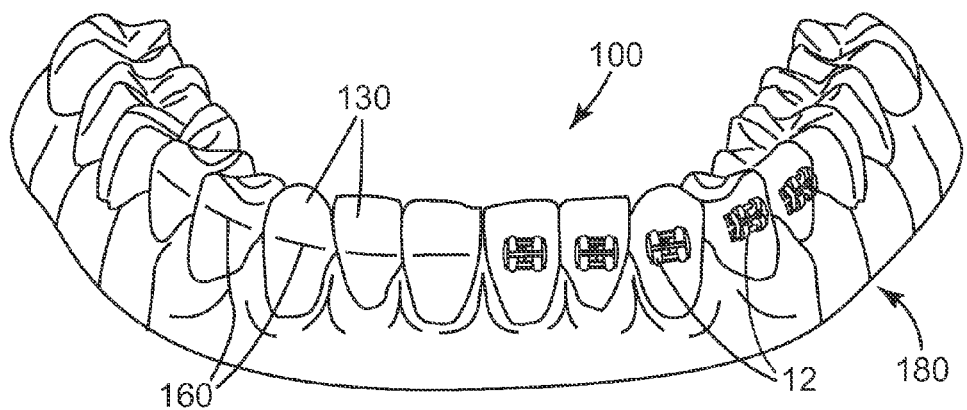
FIG. 6 is a view of the tooth structure replica illustrated in FIG. 3 after the spacer material and the tray have been removed, and additionally showing a number of orthodontic appliances that have been placed in predetermined positions on the replica.

Next, a determination is made, using any of a variety of methods, of the proper intended position of each appliance on replica teeth 130, corresponding to the ultimate desired position of the same appliance on the corresponding patient's tooth. For example, a pencil mark can be made across the labial surface of each replica tooth 130, typically with the assistance of a height gauge such as ones available as MBT bracket positioning gauge or Boone bracket positioning gauge, both from 3M Unitek, Monrovia, Calif. The pencil line is drawn across the labial surface of each replica tooth 130 to serve as a location guide for placement of the archwire slot (e.g., designated by the numeral 17 in FIG. 1A) of each orthodontic appliance (such as an orthodontic bracket). In FIG. 6, pencil lines are designated by the numeral 160. Markers may be used to register virtual and physical dental arches, as described in U.S. Patent Publication No. 2007/0031774.

Next, orthodontic appliances 12 (for example, orthodontic brackets) as selected by the practitioner are placed on the corresponding replica teeth 130, typically in positions such that the archwire slot of each appliance 12 is approximately aligned with the respective pencil line 160. In some embodiments, the orthodontic appliances 12 are precoated appliances that have a hardenable composition (typically in the form of a light-curable orthodontic adhesive) applied by the manufacturer adjacent or, alternatively, on the base of each appliance 12. Such precoated appliances are described in U.S. Pat. No. 5,015,180 (Randklev), U.S. Pat. No. 5,172,809 (Jacobs et al.), U.S. Pat. No. 5,354,199 (Jacobs et al.), and U.S. Pat. No. 5,429,229 (Chester et al). The appliances 12 can be made of any suitable material such as metal (e.g., stainless steel), ceramic (e.g., translucent polycrystalline alumina) or plastic (e.g., translucent polycarbonate). In some embodiments, the orthodontic appliances are made of material that transmits actinic radiation. In various embodiments, the orthodontic appliances are translucent or transparent. In some embodiments, the appliances have a base and at least one passageway extending through the base, whereby the passageway can receive an element that transmits actinic radiation, as described in U.S. Pat. No. 6,482,002 (Jordan et al.). If orthodontic appliances 12 are not precoated by the manufacturer with a hardenable composition, a hardenable composition can be applied adjacent or, alternatively, on the base of each appliance 12. Once orthodontic appliances 12 have been placed on replica teeth 130, appliances 12 are shifted as needed to align the central occlusal-gingival axis of appliance 12 with the long axis of each replica tooth 130 and to place the archwire slot of each bracket directly over underlying pencil line 160. Alternatively, a positioning gauge can be used to precisely position the archwire slot of each appliance 12 the distance specified above from the occlusal edge of the corresponding replica tooth 130.

Alternatively, the appliances can be placed on the teeth by means of robotic equipment. For example, the robotic equipment can include a gripping arm that is programmed to pick an appropriate appliance from a set of appliances and place the selected appliance on the appropriate tooth. The robotic arm then proceeds to grasp another appliance for placement on another tooth. Optionally, the path of movement of the robotic arm and the ultimate position of the placed orthodontic appliance 12 are determined by computer software that has access to digital data representing a virtual model of replica 100. The software can include subprograms for selecting orthodontic appliances, analyzing malocclusions and/or predicting tooth movement and final positions of the teeth. An example of software for choosing appliances is described in U.S. Pat. No. 7,155,373 (Jordan et al.).

Next, the practitioner applies firm pressure to each orthodontic appliance 12, optionally using a scaler or other hand instrument to apply force to archwire slot 17 of each appliance 12, in order to ensure that appliance 12 is firmly seated on replica tooth 130. A tool such as a dental explorer, a dental scaler, a swab, or a brush can then be used to remove any excess hardenable composition that might have been extruded near the periphery of the base of appliance 12 during seating. In some embodiments, any excess hardenable composition can be removed after the hardenable composition has been partially hardened.

In the Figures, hardenable composition 16 and partially hardened hardenable composition 36 are not necessarily drawn to scale. The use of hardenable composition 16 in the form of a light curable adhesive is advantageous because an orthodontist's assistant or a lab technician can carry out the steps described immediately above and then give replica 100 to the orthodontist or to a lab supervisor. The orthodontist or supervisor can then make a final check as to the precise placement of each orthodontic appliance 12 on the corresponding replica tooth 130 before the hardenable composition 16 is partially hardened. As one example, a number of replicas 100 can be prepared and stored in an opaque container (i.e., a container that does not transmit actinic radiation) such as a black plastic box until reviewed by the orthodontist or supervisor. In this manner, the orthodontist or supervisor can review the placement of appliances 12 on a number of different replicas 100 at a convenient time, without premature partial hardening of hardenable composition 16.

Once the accuracy of the orthodontic appliance position has been confirmed, a source of actinic radiation is directed toward hardenable composition 16. As the actinic radiation reaches the hardenable composition, a photopolymerization reaction is initiated and the hardenable composition 16 partially hardens. Suitable sources of actinic radiation include hand-held light curing units as well as stationary curing chambers. The actinic radiation is directed to the hardenable composition for a time sufficient to partially harden hardenable composition 16. That is, sufficient actinic radiation is directed to the hardenable composition to partially harden it. The partially hardened hardenable composition is designated by the numeral 36.

An example of a suitable curing chamber is a visible light curing system available under the trade designation TRIAD 2000 from DENTSPLY International, York, Pa. Preferably, the curing chamber is sufficiently large to contain a number of replicas 100 so that the hardenable composition 16 on a number of replicas 100 can be partially hardened simultaneously. In such a chamber, the light source and the replicas 100 preferably move relative to each other while the light source is activated to facilitate partial hardening of each portion of (or across the extent of) hardenable composition 16.

If orthodontic appliances 12 are made of metal or other opaque material, replica 100 can be exposed to the curing light for a relatively long period of time to ensure that hardenable composition 16 has partially hardened to a sufficient extent. The length of time can vary depending on the intensity of the actinic radiation. As an alternative to the light curing chambers mentioned above, a hand-held curing unit can be used, such one available under the trade designation ORTHOLUX LED curing light from 3M Unitek, Monrovia, Calif.

The use of transparent or translucent materials (i.e., materials that transmit actinic radiation) to make replica 100 is especially advantageous in instances where orthodontic appliances 12 are made of opaque materials, since the actinic radiation can be transmitted through replica 100 for partially hardening portions of hardenable composition 16 that are located adjacent the middle of the appliance base. Those portions might otherwise not receive sufficient actinic radiation to enable the hardenable composition to partially harden across its extent. The unhardened or insufficiently partially hardened portions of the hardenable composition might then shift and deform as the appliance is pulled away from the replica and, as a result, might not retain a shape or contour that matches the configuration of corresponding areas of the replica or of the tooth structure that it replicates. Actinic radiation can include wavelengths in the visible range (i.e., about 400 nm to about 750 nm), ultraviolet range (i.e., about 4 nm to about 400 nm), infrared range (i.e. about 750 nm to about 1000 micrometers) or any combination thereof, in accordance with the type of initiator contained in hardenable composition 16.

Actinic radiation passing through replica 100 can travel along one or more paths. For example, the actinic radiation can be emitted from a source that is located on the lingual side of replica 100 directly opposite the orthodontic appliance and travel in a buccolabial direction toward the appliance base. As another example, the source of actinic radiation can be offset from a position directly opposite the appliance, and positioned such that the actinic radiation follows along a path that extends at an angle relative to a buccolabial-lingual reference axis. As used herein, a path "through" the replica is not limited to paths that enter and exit on opposite sides of the replica, and also include paths that enter and exit on the same side of the replica.

In some embodiments, replica 100 does not consist entirely of a material that transmits actinic radiation. For example, replica 100 can include a core or other section that is made of a material opaque to actinic radiation, and a layer of a light-transmitting material is then applied over the core or other section. In that instance, a layer of reflective material can be placed between the layer of light-transmitting material and the core or other section in order to facilitate the transmission of actinic radiation to hardenable composition 16.

In some embodiments, an orthodontic archwire can be placed in the slots of appliances 12 and ligated in place. This step serves to further reduce the patient's time that is subsequently spent in the chair.

Figure 7:
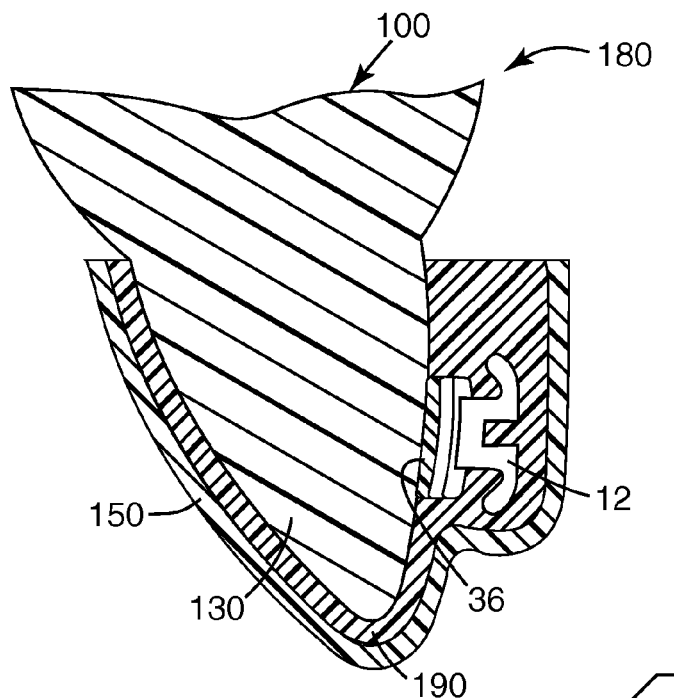
FIG. 7 is an enlarged side cross-sectional view of one of the replica teeth and appliances depicted in FIG. 6, and additionally showing a quantity of matrix material which has been placed between the replica and the tray shown in FIG. 5 after the replica and the tray have been inverted to make a transfer assembly.

Replica 100, together with orthodontic appliances 12 (and the archwire, if any), represent a treatment model 180 of an orthodontic patient set-up as shown in FIG. 6. A matrix material can then be applied, either to model 180 or to the channel of tray 150. Then, model 180 is positioned in tray 150 such that the matrix material is received in the channel of tray 150 and between tray 150 and model 180. The matrix material is then allowed to set. In FIG. 7, the matrix material is designated by the numeral 190 and surrounds appliance 12 as well as the labial and lingual surfaces of replica tooth 130. In this embodiment, the transfer apparatus (comprising tray 150) holds appliance 12.

In some embodiments, the matrix material has a relatively low viscosity before setting. In this manner, matrix material 190 is able to substantially penetrate into various recesses, cavities and other structural features of appliance 12 so that a secure connection between appliance 12 and matrix material 190 can be established. An example of a suitable matrix material is a silicone material available under the trade designation RTV615 from General Electric Co., Wilton, Conn. Alternatively, the matrix material 190 can comprise a dental impression material or a bite registration material. Suitable materials include poly(vinyl siloxane) impression material, such as those available under the trade designation MEMOSIL 2 from Heraeus Kulzer Inc., Armonk, N.Y., or PEPPERMINT SNAP CLEAR BITE registration material from Discus Dental Inc., Culver City, Calif. In some embodiments, matrix material 190 transmits actinic radiation.

Once matrix material 190 has set, tray 150, together with matrix material 190 and orthodontic appliances 12 with partially hardened hardenable composition 36 thereon, are detached from replica 100. The use of the release agent as described above can facilitate detaching of appliances 12 from the corresponding replica teeth 130. Excess material of tray 150 and excess matrix material 190 can then be trimmed as desired. The resultant transfer assembly 44 (comprising a transfer apparatus in the form of tray 150, matrix material 190, and appliances 12 having partially hardened hardenable composition 36 thereon) is shown in cross-sectional view in FIG. 8.

Figure 8:
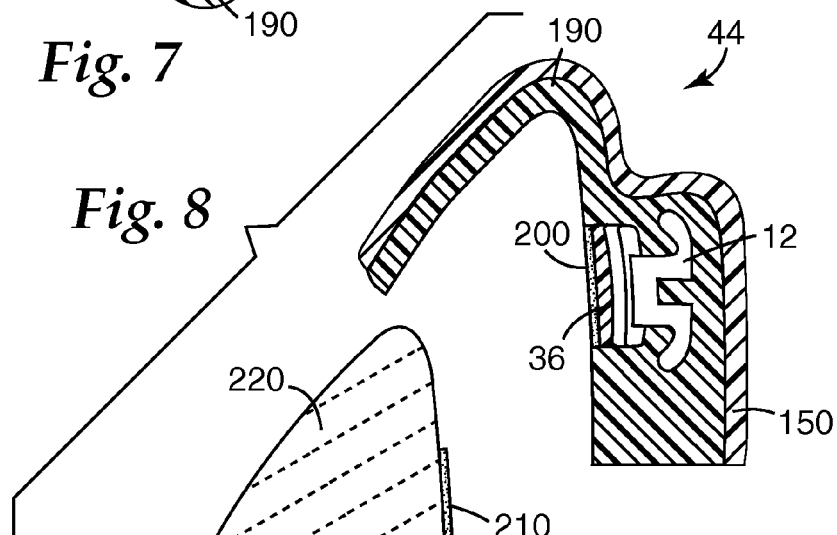
FIG. 8 is an enlarged side cross-sectional view showing the transfer assembly (comprising a transfer apparatus in the form of a transfer tray, an orthodontic appliance, a partially hardened hardenable composition, and a component of a bonding adhesive) advancing toward one of the patient's teeth.
Figure 8:
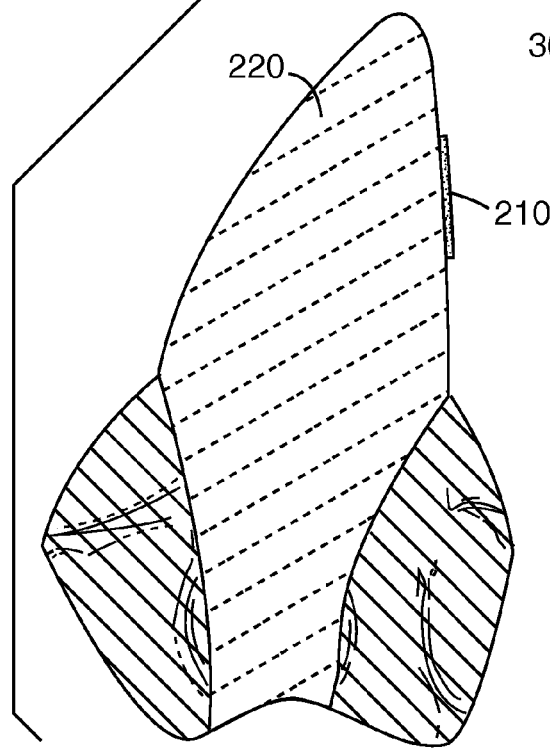

Methods to identify patient-specific articles can be used, including the use of radio frequency identification (RFID) tags, as described in U.S. Patent Application Publication No. 2006/0134580. Typically, some of the steps described above are carried out between patient visits to an orthodontist's office. Once the patient has returned to the office, the patient's teeth that are to receive orthodontic appliances are isolated using cheek retractors, tongue guards, cotton rolls, dry angles and/or other articles as needed. The teeth are then thoroughly dried using pressurized air from an air syringe. In some embodiments, etching solution (such as one available under the trade designation TRANSBOND XT etching gel from 3M Unitek, Monrovia, Calif.) is then dabbed onto the teeth in the general area that is to be covered by appliances 12. After the etching solution has remained on the selected tooth surfaces for a period of time sufficient to etch the tooth, the solution is rinsed away from the teeth with a stream of water. The patient's teeth are then dried, for example by the application of pressurized air from an air syringe, and excess water is removed by suction. Next, a bonding adhesive is applied to the partially hardened hardenable composition 36 and/or the selected areas of the patient's teeth. In some embodiments, the adhesive is a one-component bonding adhesive. In other embodiments, such as illustrated in FIG. 8, the adhesive is a two-component bonding adhesive. For example, first component 200 can be a moisture-insensitive primer (such as one available under the trade designation TRANSBOND MIP from 3M Unitek, Monrovia, Calif.), and second component 210 can be a self-etching primer (such as one available under the trade designation TRANSBOND PLUS from 3M Unitek). If a self-etching primer is used, the etching step described above is typically omitted. The first component 200 is applied to the partially hardened hardenable composition 36 and the second component 210 is applied to the area of the patient's tooth that is to receive the orthodontic appliance 12. In FIG. 8, the patient's tooth is designated by the numeral 220. Other examples of suitable two-component chemical curing adhesives include those available under the trade designation SONDHI RAPID-SET indirect bonding adhesive, UNITE bonding adhesive, and CONCISE orthodontic adhesive, from 3M Unitek, Monrovia, Calif. Alternatively, a resin-modified glass ionomer cement can be used. Alternatively, a photocurable bonding adhesive can be used, such as one available under the trade designation TRANSBOND light cure adhesive from 3M Unitek.

After first component 200 has been applied to partially hardened hardenable composition 36 and second component 210 has been applied to the corresponding area of the patient's tooth 220, assembly 44 is then positioned over the corresponding teeth and seated, optionally with a swinging, hinge-like motion. Since the shape of the cavity of matrix material 190 matches the shape of the underlying teeth, appliances 12 are simultaneously seated against underlying teeth 220 at the same locations as the previous position of appliances 12 on replica 100. Preferably, pressure is then applied to the occlusal, labial and buccal surfaces of tray 150 until the bonding adhesive has sufficiently hardened.

Once the bonding adhesive has sufficiently hardened, tray 150 is removed from the patient's dental arch. Typically, tray 150 is first separated from matrix material 190, which remains in place over the dental arch along with orthodontic appliance 12. Next, matrix material 190 is detached from appliance 12. Optionally, a hand instrument such as a scaler can be used to help hold each appliance 12 against the surface of the respective tooth 220 of the patient as matrix material 190 is peeled away from appliance 12. As another option, tray 150 can be separated from matrix material 190 before the bonding adhesive has hardened. This option is particularly useful when the bonding adhesive is a light-curable bonding adhesive. In some embodiments, tray 150 may be provided with, for example, a flexible cord to fracture matrix material 190, as described in U.S. Pat. No. 7,020,963 (Cleary et al).

Once matrix material 190 has been detached from orthodontic appliance 12, an archwire is placed in the slots of appliances 12 and ligated in place. Suitable ligation devices include elastic O-rings as well as sections of wire that are tied in a loop around appliances 12. Alternatively, appliances 12 can be self-ligating appliances that include a latch for releasably engaging the archwire such as those described in U.S. Pat. No. 6,302,688 (Jordan et al.) and PCT International Patent Application Publication No. 02/089693.

Advantageously, the partially hardened hardenable composition 36 provides a "custom base" (having a bonding surface) for base 14 of the corresponding orthodontic appliance 12. In some embodiments, the contour of this bonding surface closely matches the shape of the patient's tooth surface and consequently facilitates the subsequent bond (using bonding adhesive components 200, 210) that is established between appliance 12 and tooth 220. In other embodiments, the contour of this bonding surface is a negative replica of at least a portion of the tooth structure. The custom base (comprising partially hardened hardenable composition 36) advantageously reduces the likelihood that appliance 12 will become unintentionally detached from the tooth during the course of treatment.

When replica 100 transmits actinic radiation a number of advantages are provided. The light-transmitting replica 100 enables actinic radiation to reach substantially all portions of hardenable composition 16, including portions near the middle of the orthodontic appliance base that might otherwise be difficult to reach. As a consequence, substantially all portions of the hardenable composition 16 can be partially hardened before appliance 12 is detached from replica 100, and the configuration, shape, or contour of the resulting bonding surface is not disturbed. The resulting bonding surface has a configuration, shape, or contour that precisely matches the shape of the corresponding replica surface, i.e., a contour of a negative replica of at least a portion of the tooth structure.

Moreover, the use of spacer material 110, 120 facilitates the use of a matrix material having a relatively low viscosity, such as a matrix material having a liquid consistency. Typically, tray 150 is relatively stiff, and consequently maintains its shape during forming of matrix material 190. As a result, transfer assembly 44 can be assembled such that tray 150 does not directly contact the patient's teeth or gingival tissue. Instead, only matrix material 190 comes into contact with the patient's teeth, so that a close, matching fit with the oral structure is provided.

In some embodiments, the transfer apparatus can be used for bonding only a single orthodontic appliance to a patient's tooth. For example, a portion of the transfer apparatus described above can be used to bond a single appliance to a single tooth subsequent to the time that other appliances are bonded, such as in instances where access to the tooth is initially hindered by other teeth. As another example, a portion of the transfer apparatus described above can be used to re-bond an orthodontic appliance that has unintentionally debonded from the tooth, or to bond a new appliance to a tooth to replace the original appliance.

Optionally, a transfer apparatus can include one or more occlusal stop members that engage one or more occlusal sections of the patient's dental arch as the appliance or appliances are positioned on the patient's tooth structure. Each of the occlusal stop members helps to accurately position the appliance with respect to the patient's tooth structure. In some embodiments, the stop members can be made of, for example, an orthodontic or a dental adhesive, a dental restorative material, or a bite registration material. These and other embodiments are disclosed in, for example, U.S. Patent Application Publication No. 2006/0223021 (Cinader et al.).

Optionally, a transfer apparatus in the form of a transfer tray can be made using rapid prototyping as disclosed in, for example U.S. patent application Ser. No. 11/689,869.

Optionally, digital data of a patient's teeth (and, optionally, adjacent gingival tissue) can be obtained using, for example, an intra-oral scanner or a cone beam computed tomography scanner. The digital data can be used to create a virtual model on which a practitioner can place and position virtual orthodontic appliances using a computer. Further digital design can include design of virtual guides, a transfer appliance molding vessel, and occlusal stop members. A dental arch replica can then be prepared using rapid prototyping, as described in U.S. patent application Ser. No. 11/689,845.

In other embodiments, structures can be added to tray 150 to provide moisture control during indirect bonding of an orthodontic appliance to a tooth structure, as described in U.S. Published Patent Application Nos. 2007/0287120 and 2007/0287121.

EXAMPLES

Bond Strength Test Procedure

To determine the bond strength of an orthodontic bracket to a bovine tooth, each tooth (with bracket bonded to it) was mounted in methacrylate resin by placing the tooth in the resin and allowing the resin to cure. The Bond Strength Test was performed by engaging 0.50 millimeter round stainless steel wire loop under the occlusal tie wing of the bracket. A load was applied (shear/peel) using a load tester (Instron, Norwood, Mass.) at a rate of 5 millimeters per minute. The maximum force (in units of Newtons) to remove the bracket from the tooth was recorded as the bond strength. The bond strength value reported in Examples 1 and 2 and Comparative Example 1 are averages of 28 measurements, 33 measurements, and 33 measurements, respectively.

Example 1

Bond Strength

A stone model representative of a human dental arch was used to prepare a mold by first forming clear mouthguard thermal forming material (available from Great Lakes Orthodontics, Ltd., Tonawanda, N.Y.) over the model. The mold was removed from the model and was filled with dental impression material (available under the trade designation POSITION PENTA QUICK VPS from 3M ESPE, St. Paul, Minn.). Eight to fourteen bovine teeth (depending on the size of the individual teeth) were immediately set into the impression material in the mold, occlusal surfaces down and labial surfaces aligned with the outside wall of the mold. After the impression material had set, an orthodontic stone mixture (available from Whip Mix Corp., Louisville, Ky.) was poured into the mold (to cover and embed the exposed portions of the teeth) and was allowed to set. The mold was removed from the set stone with embedded bovine teeth (the "dental arch") and the excess stone was removed from the teeth using a sickle style cement removal tool, an orthodontic bracket positioning tool, and a toothbrush.

An impression of the dental arch was made using dental impression material (available under the trade designation POSITION PENTA QUICK VPS from 3M ESPE, St. Paul, Minn.) and trays (available under the trade designation 3M ESPE DIRECTED FLOW IMPRESSION TRAY from 3M ESPE, St. Paul, Minn.). After the set impression material was removed from the dental arch, the periphery of the impression was reinforced using a dental impression putty obtained under the trade designation EXPRESS STANDARD PUTTY from 3M ESPE, St. Paul, Minn. The impression was then dried in an oven at approximately 60° C. for approximately 4 hours. The impression was used to create an epoxy model (a replica of the "dental arch") by pouring a mixture of an epoxy resin and a hardener (available under the trade designation F-82 (resin) and UCE-302 (hardener), both available from United Resin Corp., Royal Oak, Mich., and mixed according to directions provided by the manufacturer). The resultant epoxy model transmitted actinic radiation.

Using a method essentially as described in, for example, U.S. Pat. No. 7,020,963 (Cleary et al.), silicone spacers were placed on the replica teeth of the epoxy model and a transfer apparatus in the form of a transfer tray was then vacuum formed over the model from a polycarbonate sheet (available under the trade designation MAKROLON from Bayer MaterialScience AG, Leverkusen, Germany). The tray was then removed from the model and the silicone spacers were removed from the replicated teeth of the model. A thin layer of a release agent (a water soluble poly(vinyl alcohol) available under the trade designation PA0810 from PTM&W Industries, Inc., Santa Fe Springs, Calif.) was applied to the model. A hardenable composition in the form of an orthodontic adhesive (TRANSBOND XT, 3M Unitek, Monrovia, Calif.) was applied via syringe to the bases of orthodontic brackets (available under the trade designation VICTORY SERIES from 3M Unitek, Monrovia, Calif.). Sufficient hardenable composition was applied to each bracket base to cover the entire base and provide a layer of composition that appeared to be free of voids. Each bracket was manually pressed onto a replica tooth of the model and excess hardenable composition was manually removed from the replica tooth surface. The hardenable composition was partially hardened by exposing it to actinic radiation from an orthodontic curing light (available under the trade designation ORTHOLUX LED from 3M Unitek, Monrovia, Calif.) for 5 seconds. The exposure was made from the lingual side of the model, i.e., the actinic radiation was transmitted through the model to the hardenable composition. Then, thin pads of an impression material (EXPRESS BITE, 3M ESPE, St. Paul, Minn.) were formed into a thin roll and were pressed on the occlusal surfaces of the replica teeth, pressing toward the lingual side of the replica teeth.

Both parts of a curable two-part silicone (available under the trade designation RTV615, from General Electric Co., Wilton, Conn.) were combined in a container that was then placed in a bell jar which was then evacuated to remove air bubbles entrained in the mixture. The silicone was then poured into the polycarbonate transfer apparatus (in the form of a transfer tray), and the epoxy model (with the orthodontic brackets affixed to the replica teeth) was placed in the tray so that each bracket and the incisal edge of each replica tooth was covered with silicone. This assembly was then placed in an oven at a temperature of approximately 60° C. for approximately 4 hours to allow the silicone to set. The tray and cured silicone were then trimmed to a level near the gingival tie wings of the brackets.

This assembly was then soaked in water in an ultrasonic bath for approximately 60 minutes. The transfer tray/brackets assembly was removed from the model, using a dental tool as necessary to pry the brackets from the replica teeth. The partially hardened hardenable composition on the base of each bracket was steam cleaned and was then rinsed with water to remove any residual poly(vinyl alcohol) from the composition. The transfer tray/bracket assembly was then dried in an oven at approximately 60° C. for approximately 1 hour.

The embedded bovine teeth in the dental arch were cleaned using an aqueous slurry of pumice, then they were rinsed with water, using a toothbrush as necessary to remove the pumice, and dried with a stream of air. A self etching primer (available under the trade designation TRANSBOND PLUS SELF ETCHING PRIMER from 3M Unitek, Monrovia, Calif.) was applied to the teeth, which were then dried using a stream of air. A coating of a primer (TRANSBOND XT, 3M Unitek, Monrovia, Calif.) was applied to the surface of the partially hardened hardenable composition on the base of each bracket, and the transfer tray/bracket assembly was placed and fully seated on the dental arch such that no gaps were observed along the incisal edges. The partially hardened hardenable composition between each bracket and a corresponding tooth was further hardened using an orthodontic curing light (available under the trade designation ORTHOLUX LED from 3M Unitek, Monrovia, Calif.) for 10 seconds from each of the mesial and distal directions. The transfer tray was removed, and the cured silicone was carefully peeled from the brackets. The dental arch was then submerged in water overnight.

The bovine teeth were then removed from the stone by using a chisel and hammer on the lingual side of the teeth. The bond strength of the brackets was determined using the Bond Strength Test described above. The data are given in Table 1.

Example 2

The procedure of Example 2 was carried out essentially as described in Example 1, except that the hardenable composition was partially hardened by exposing it to actinic radiation from an orthodontic curing light for 10 seconds. The data are given in Table 1.

Comparative Example 1

The procedure of Example 1 was carried out essentially as described in Example 1, except that the hardenable composition was hardened by exposing it to actinic radiation from an orthodontic curing light for 20 seconds. The hardened composition of Comparative Example 1 was considered to be fully cured. The bond strength data are given in Table 1.

TABLE 1

Bond Strength Data for Examples 1-2 and Comparative Example 1.

| Example | Curing Time | Bond Strength |
|---|---|---|
| Example 1 | 5 seconds | 173 N |
| Example 2 | 10 seconds | 149 N |
| Comparative 1 | 20 seconds | 122 N |

Examples 3-5

Degree of Cure

The compositions of Examples 1-2 and Comparative Example 1 were analyzed spectrophotometrically to determine the degree of cure by calculating the ratio of a measure of unreacted reactive chemical groups (in these Examples, methacrylate groups) in each exemplary composition to a measure of unreacted reactive chemical groups in the composition of Comparative Example 1. The composition of Comparative Example 1 was considered to be fully cured. Using attenuated total reflectance FT infrared spectrophotometry (using a model HYPERION 2000 FT-IR microscope and a germanium ATR objective, available from Bruker Optics, Inc., Billerica, Mass.), the infrared spectrum of each of the compositions of Examples 1-2 and Comparative Example 1 was measured. Three samples of each of the compositions were analyzed by first calculating a first ratio of absorbances at 1637 $cm^{-1}$ and 1510 $cm^{-1}$ of each sample. Then, the ratio of the first ratio of each of the compositions of Examples 1-2 to the first ratio of the composition of Comparative Example 1 was calculated and was multiplied by 100 to provide the degree of cure (as a percentage) for each exemplary composition. As noted above, composition of Comparative Example 1 was considered to be fully cured; the degree of cure of Comparative Example 1 was considered to be 100%.

TABLE 2

Degree of Cure Data for Examples 3-5.

| Example | Composition | Curing Time | Degree of Cure |
|---|---|---|---|
| 3 | Example 1 | 5 seconds | 27.7% |
| 4 | Example 2 | 10 seconds | 93.6% |
| 5 | Comparative 1 | 20 seconds | 100% |

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of bonding an orthodontic article to a tooth structure comprising:
   a) applying a hardenable composition to the base of an orthodontic appliance whereby the hardenable composition extends across the base;
   b) partially hardening the hardenable composition to provide a partially hardened hardenable composition, the partially hardened hardenable composition being less than 95 percent cured and having a contour of a negative replica of at least a portion of the tooth structure;
   c) applying a bonding adhesive to the partially hardened hardenable composition whereby the bonding adhesive extends across the partially hardened hardenable composition; and
   d) advancing the orthodontic appliance with the partially hardened hardenable composition toward the tooth structure.

2. The method of claim 1 wherein the base has a contour of a negative replica of at least a portion of the tooth structure.

3. The method of claim 1 wherein the step of partially hardening the hardenable composition comprises directing actinic radiation to the hardenable composition.

4. The method of claim 1 wherein the step of advancing comprises holding the appliance with a transfer apparatus.

* * * * *